United States Patent [19]
VanCott

[11] Patent Number: 5,202,248
[45] Date of Patent: Apr. 13, 1993

[54] METHOD FOR CLONING AND PRODUCING THE NCO I RESTRICTION ENDONUCLEASE AND METHYLASE

[75] Inventor: Elizabeth M. VanCott, Malden, Mass.

[73] Assignee: New England Biolabs, Inc., Beverly, Mass.

[21] Appl. No.: 608,228

[22] Filed: Nov. 2, 1990

[51] Int. Cl.$^5$ .................... C12N 9/22; C12N 15/55
[52] U.S. Cl. .................... 435/199; 435/143; 435/252.33; 435/320.1; 536/23.2
[58] Field of Search .................... 435/199, 193, 320.1, 435/252.33; 536/27

[56] References Cited

U.S. PATENT DOCUMENTS

| | | | |
|---|---|---|---|
| 4,983,522 | 1/1991 | Barsomian et al. | 435/172.3 |
| 4,983,542 | 1/1991 | VanCott et al. | 435/172.3 |
| 4,987,074 | 1/1991 | Lunnen et al. | 435/172.3 |

FOREIGN PATENT DOCUMENTS 193413 3/1986 European Pat. Off. .

OTHER PUBLICATIONS

VanCott et al. (1988) Gene 74, 55-59.
Roberts, R. J. (1985) Nuc. Acids Res., r165, r185, r196.
Endow, et al., J. Mol. Biol. 112:521 (1977).
Waalwijk, et al., Nucleic Acids Res. 5:3231 (1978).
Gingeras, et al., Proc. Natl. Acad. Sci. U.S.A. 80:402 (1983).
Mann, et al., Gene 3:97-112 (1978).
Kosykh, et al., Molec. Gen. Genet. 178: 717-718 (1980).
Walder, et al., Proc. Nat. Acad. Sci. U.S.A. 78:1503-1507 (1981).
Bougueleret, et al., Nucleic Acids Res. 12:3659-3676 (1984).
Theriault & Roy, Gene 19:355-359 (1982).
Blumenthal, et al., J. Bacteriol 164:501-509 (1985).
Howard, et al., Nucleic Acids Res. 14:7939-7951 (1988).
Wilson, Gene 74:281-289 (1988).
Wilson, Trends in Genetics 4:314-318 (1988).
Lunnen, et al., Gene 74:25-32 (1988).
Chandrasegeran, et al., Structure and Expression; Adenine Press vol. I pp. 149-156 (1988).
Brooks, et al., Gene 74:13 (1988).
Birnboim & Doly Nucleic Acids Res. 7:1513 (1979).
Southern E. J. Mol. Bio. 98:503 (1975).

Primary Examiner—Charles L. Patterson, Jr.
Attorney, Agent, or Firm—Gregory D. Williams; David G. Conlin

[57] ABSTRACT

The present invention is directed to a method for cloning and producing the NcoI restriction endonuclease by 1) introducing the restriction endonuclease gene from *N. corallina* into a host whereby the restriction gene is expressed; 2) fermenting the host which contains the plasmid encoding and expressing the NcoI restriction endonuclease activity, and 3) purifying the NcoI restriction endonuclease from the fermented host which contains the plasmid encoding and expressing the NcoI restriction endonuclease activity.

6 Claims, 5 Drawing Sheets

METHOD FOR CLONING AND PRODUCING THE NCO I RESTRICTION ENDONUCLEASE AND METHYLASE

BACKGROUND OF THE INVENTION

The present invention relates to recombinant DNA which encodes the NcoI restriction endonuclease and modification methylase, and to methods for the production of these enzymes from the recombinant DNA.

Many bacteria contain systems which guard against invasion of foreign DNA. Bacterial cells contain specific endonucleases that make double-strand scissions in invading DNA unless the DNA has been previously modified, usually by the corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Three distinct types of R-M systems have been characterized on the basis of the subunit compositions, cofactor requirements, and type of DNA cleavage. Type I R-M systems are the most complex. The endonuclease typically contains three different types of subunits and require $Mg^{++}$, ATP, and S-adenosyl-methionine for DNA cleavage. Their recognition sites are complex, and DNA cleavage occurs at non-specific sites anywhere from 400-7000 base pairs from the recognition site.

Type III R-M systems are somewhat less complex. The endonuclease of type III R-M systems contain only two types of subunits, and although $Mg^{++}$ and ATP are required for DNA cleavage, S-adenosyl-methionine stimulates enzymatic activity without being an absolute requirement. DNA cleavage occurs distal to the recognition site by about 25-27 base pairs.

Type II R-M systems are much simpler than either types I or III. The endonuclease only contains one subunit, and only $Mg^{++}$ is required for DNA cleavage. Moreover, the DNA cleavage site occurs within or adjacent to the enzyme's recognition site. It is this class of restriction endonucleases that has proved most useful to molecular biologists.

Bacteria usually possess only a small number of restriction endonucleases per species. The endonucleases are named according to the bacteria from which they are derived. Thus, the species *Haemophilus aegyptius*, for example, synthesizes three different restriction endonucleases, named Hae I, Hae II and Hae III. These enzymes recognize and cleave the sequences (AT)GGCC(AT), PuGCGCPy and GGCC respectively. *Escherichia coli* RY13, on the other hand, synthesizes only one enzyme, EcoR I, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4-6 nucleotides in length. More recently, recognition endonucleases having recognition sequences of 7-8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes." Some restriction endonucleases have degenerate or relaxed specificites in that they can recognize multiple bases at the same positions. EcoRI, which recognizes the sequence GAATTC is an example of a restriction endonuclease having a symmetrical relationship, while HaeII, which recognizes the sequence PuGCGCPy, typifies restriction endonucleases having a degenerate or relaxed specificity. Endonucleases with symmetrical recognition sites generally cleave symmetrically within or adjacent the recognition site, while those that recognize asymmetric sites tend to cut at distance from the recognition site, typically from about 1-13 base pairs away from that site.

The second component of bacterial R-M systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or more of the nucleotides within the sequence by the addition of a methyl group. Following methylation, the recognition sequence is no longer bound or cleaved by the corresponding restriction endonuclease. The DNA of a bacterial cell is always modified by virtue of the activity of its modification methylase, and it is therefore insensitive to the presence of the endogenous restriction endonuclease. It is only unmodified, and therefore identifiably foreign DNA that is sensitive to restriction endonuclease recognition and attack.

More than 1000 different restriction endonucleases have been isolated from bacterial strains, and many share common specificites. Restriction endonucleases which recognize identical sequences are called "isochizomers." Although the recognition sequences of isochizomers are the same, they may vary with respect to site of cleavage (e.g., Xma I V. Sma I Endow et al., *J.Mol.-Biol.* 112:521 (1977) Waalwijk et al., *Nucleic Acids Res.* 5:3231 (1978)) and in cleavage rate at various sites (Xho I v. Pae R7I Gingeras et al., *Proc. Natl. Acad. Sci U.S.A.* 80:402 (1983)).

With the advent of genetic engineering technology, it is now possible to clone genes and to produce the proteins and enzymes that they encode in greater quantities than are obtainable from their natural sources by conventional purification techniques.

Type II restriction-modification systems are being cloned with increasing frequency. Four methods are being used to clone R-M systems into *E. coli*: (1) subcloning of natural plasmids; (2) selection based on phage restriction; (3) selection based on vector modification; and (4) multi-step isolation.

The first cloned systems used bacteriophage infection as a means of identifying or selection restriction endonuclease clones (Hha II: Mann, et al., Gene 3: 97-112, (1978); EcoR II: Kosykh, et al., Molec. Gen. Genet. 178: 717-719, (1980); Pst I: Walder, et al., Proc. Nat. Acad. Sci. USA 78: 1503-1507, (1981)). Since the presence of R-M systems in bacteria enables them to resist infection by bacteriophages, cells that carry cloned R-M genes can, in principle, be selectively isolated as survivors from libraries that have been exposed to phage. This method has been found, however, to have only limited value. Specifically, it has been found that cloned R-M genes do not always manifest sufficient phage resistance to confer selective survival.

Subcloning of natural plasmids involves transferring systems initially characterized as plasmid-borne into *E. coli* cloning plasmids (EcoRV: Bougueleret, et al., Nucleic Acids Res. 12: 3659-3676, (1984); PaeR7: Gingeras and Brooks, Proc. Natl. Acad. Sci. USA 80: 402-406, (1983); Theriault and Roy, Gene 19: 355-359, (1982); Pvu II: Blumenthal, et al., J. Bacteriol. 164: 501-509, (1985)). In this approach the plasmids are purified prior to digestion and ligation, so reducing the complexity of the source DNA. Isolating the system then involves sub-cloning and characterizing libraries and perfoming selections. This approach also has a number of limitations including that most R-M systems are located on the bacterial chromosome, not plasmids.

Vector modification, the most successful approach to date, is predicated on the assumption that the restriction and modification genes of a particular type II system are linked and are expressed sequentially, methylase and then endonuclease. Thus, in a population of methylase positive clones, some clones should also carry the corresponding endonuclease gene. This approach, known as methylase selection, was first used successfully by Wilson, EPO Publication No. 0193413, to clone the Hae II, Taq I, Ban I, Hind III, Hinf I, and Msp I R-M systems.

A number of R-M systems, however, have required a multi-step cloning approach. For example, during acquisition of a new R-M system, it has been found that a number of cells face an establishment problem. Unless the methylase has a head start over the endonuclease, the cell is in danger of cleaving its own cellular DNA. *E. coli* appears to cope with this problem by repairing its DNA, and is able to assimilate many cloned R-M systems without apparent trauma. Not all systems are easily assimilated however. The Dde I and BamH I R-M systems, for example, could not be cloned in a single step; rather, three steps were required (Howard et al., Nucleic Acids Res. 14:7939-7951 (1988)). There are, in fact, many systems for which only the methylase gene has been cloned. These systems may be similar to BamH I and Dde I, and may require similar approaches.

While a number of clones have been obtained by one or more of the above-described methods, see, Wilson, Gene 74, 281-289 (1988), cloning of type II R-M systems is not without difficulty. In particular, the genetics of many R-M systems have been found to be more complex, and methylase positive clones obtained by, for example, vector modification have not yielded the corresponding endonuclease gene. See, Wilson, Trends in Genetics 4, 314-318 (1988); Lunnen et al., Gene 74, 25-32 (1988). In fact, numerous obstacles are encountered in the process of cloning R-M systems using vector modification. For example, in some systems, the methylase and endonuclease genes may not be linked or the endonuclease used to fragment the bacterial DNA may cut either or both of the R-M genes. In other systems, such as BamH I and Dde I, the methylase may not protect sufficiently against digestion by the corresponding endonuclease, either because of inefficient expression in the transformation host, or because of the inherent control mechanism for expression of the methylase and endonuclease genes, or for unknown reasons. Modification may also be harmful to the host cell chosen for transformation. The endonuclease sought to be cloned may not be available in sufficient purity or quantity for methylase selection. In many systems, difficulties are also encountered in expressing the endonuclease gene in a transformation host cell of a different bacterial species.

In spite of the difficulties in cloning the more complex Type II R-M systems, it has been possible to obtain some endonuclease genes by modifying the vector modification selection method (see Lunnen et al., op. cit.) and/or by using a multi-step cloning approach. For example, formation of multiple libraries, construction of new cloning vectors, use of isochizomers for the methylase selection step, mapping of methylase and/or endonuclease genes to determine the corresponding DNA sequences for use as hybridization probes, and other variations to the above-described approaches have yielded a number of recalcitrant recombinant R-M systems.

However, at the outset of any type II R-M cloning project, one simply does not know which, if any, and what variations or modifications to previous approaches may be required to clone any particular R-M system. For example, the detailed genetics of the particular system is usually unknown. Type II R and M genes may be present on the genome in any of four possible arrangements. Wilson, Trends in Genetics, supra. The sizes of the enzymes, and of the corresponding genes, vary widely between one R-M system and another, as do the DNA and amino acid sequences. In fact, even isochizomeric restriction endonucleases have been found to display few similarities. Id, at 318, see also Chandrasegeran et al., *Structure and Expression*, Vol. I, pp 149-156, Adenine Press (1988).

Mechanisms of control of R and M gene expression also vary widely among type II systems. For example, expression of the endonuclease gene may be modification-dependent, as is indicated in the Ava II, Hae II, Hinf I, PstI and Xba I systems. Alternatively, the endonuclease gene may contain a large number of its own recognition sites as compared to the corresponding methylase gene, as in the Taq I system.

During transformation of cells to obtain clones carrying the target R-M system, cellular DNA is initially unmodified and consequently in danger of being digested by the target endonuclease. Transformation host cells must either contain DNA repair systems or be able to delay expression of the target endonuclease gene until modification is complete. If neither of these mechanisms is available to the transformation host, a problem is encountered in establishing the cloned genes in the host. As noted above, when establishment problems were encountered in cloning the Dde I and BamH I systems, it was necessary to introduce the methylase and endonuclease genes sequentially, to protect the DNA of the transformation host cells (Howard, K. A. et al., supra, Brooks et al., Gene 74: 13 (1988)). However, some R-M systems have resisted all attempts to clone them, and others have yielded only the methylase gene, possibly because of establishment difficulties. Wilson, Trends in Genetics 4, 317.

It has been found that transformation host cells may also contain systems that restrict foreign types of modification. For example, two systems have been identified in *E. coli* which restrict modified DNAs: the mcr system restricts DNA containing methyl-cytosine, and the mrr system restricts DNA containing methyl-adenine. It is therefore usually necessary to use E. coli strains that are defective in these systems. The presence of additional host cell restriction systems may also be responsible for the difficulties encountered in cloning of R-M systems.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA encoding the genes for the NcoI restriction endonuclease and modification methylase obtainable from *Nocardia corallina* (ATCC 19070) as well as related methods for the production of these enzymes from the recombinant DNA. This invention also relates to a transformed host which expresses the restriction endonuclease NcoI, an enzyme which recognizes the DNA sequence 5'-CCATGG-3' and cleaves between the two C residues, leaving a four base 5' overhang (Langdale, J. A., Myers, P. A., and Roberts, R. J., unpublished observations).

NcoI methylase or restriction endonuclease produced in accordance with the present invention is substantially pure and free of the contaminants normally found in restriction endonuclease preparations made by conventional techniques, e.g., as described in step 15 of Example 1.

BRIEF DESCRIPTION OF THE DRAWINGS

FIGS. 1A and 1B: Scheme for cloning and producing the NcoI restriction endonuclease:

DETAILED DESCRIPTION OF THE INVENTION

The present invention relates to recombinant DNA which encodes the NcoI restriction endonuclease and modification methylase, as well as to the enzymes produced from such a recombinant DNA. At the onset of the cloning project, it was not known which conditions would be successful in cloning the NcoI restriction-modification system, nor where the restriction and modification genes were located within such clones. The cloning results and subsequent DNA sequencing, mapping, and characterization of the clones described in FIG. 1A and Example 1 reveal the previously unknown direct pathway for cloning and expressing the NcoI restriction-modification system.

More specifically, the cloning of the NcoI restriction-modification genes from *N. corallina* into *E. coli* proved to be complicated by the discovery that unlike many other restriction-modification systems, NcoI genes do not express well in *E. coli*. Since methylase selection (the identification of methylase clones by their ability to resist and survive NcoI digestion) relies on methylase expression, selection for the NcoI methylase is not always successful. In the present invention out of a number of DNA libraries prepared, only the BclI and the Sau3A libraries were successful. Moreover, the Sau3A library was successful only on the second try.

Expression was also found to be a problem for the NcoI restriction endonuclease gene. Methylase clones from many other restriction-modification systems can be screened for restriction endonuclease activity with in vitro assays. However, none of the NcoI restriction-modification clones expressed endonuclease activity detectable by in vitro assays such as those described in the aforementioned EPO 0193413, even after concentrating crude cell extracts over phosphocellulose columns. In order to determine whether the R gene was present in the M clones, numerous additional steps were required. The steps included: a) cloning N. corallina chromosomal DNA on both sides of the M gene (PvuII, ClaI, FspI, SalI clones), b) preparing an extremely pure sample of NcoI from *N. corallina*, c) sequencing the amino-terminus of the purified restriction endonuclease protein, d) designing a corresponding DNA oligomer, and e) checking the DNA of the methylase clones for hybridization with the oligomer. In this manner, the BclI methylase clones and possibly the PvuII or Cla clones, which on the downstream side of the M gene are only subsets of the BclI clone, were found to carry the R gene, whereas none of the other methylase clones were found to carry the R gene. In order to obtain NcoI restriction endonuclease activity, the R gene was sequenced, and the beginning of the gene was reconstructed.

Figure 1A:
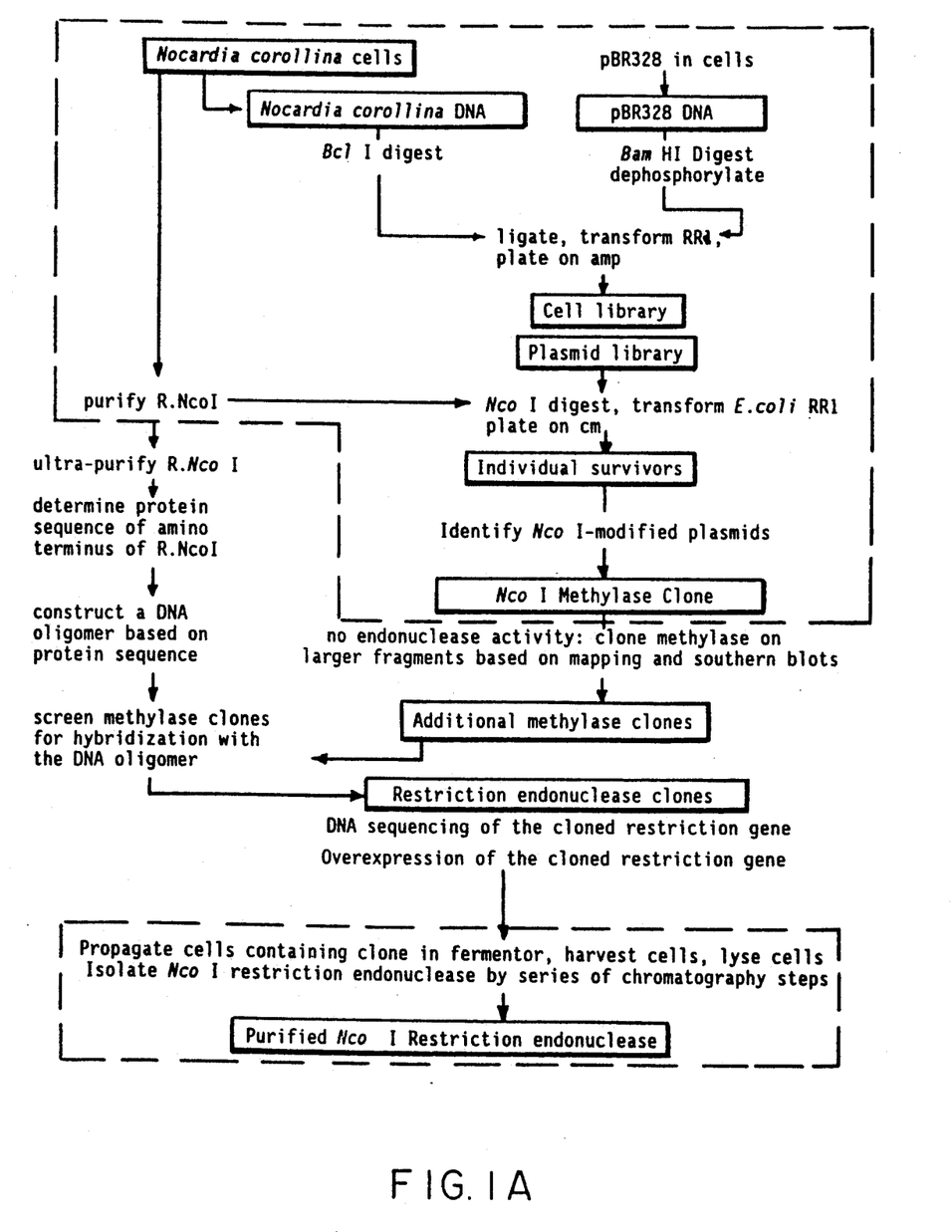
FIG. 1A illustrates the procedures for determining the preferred method for cloning and producing the NcoI restriction endonuclease.
Figure 1B:
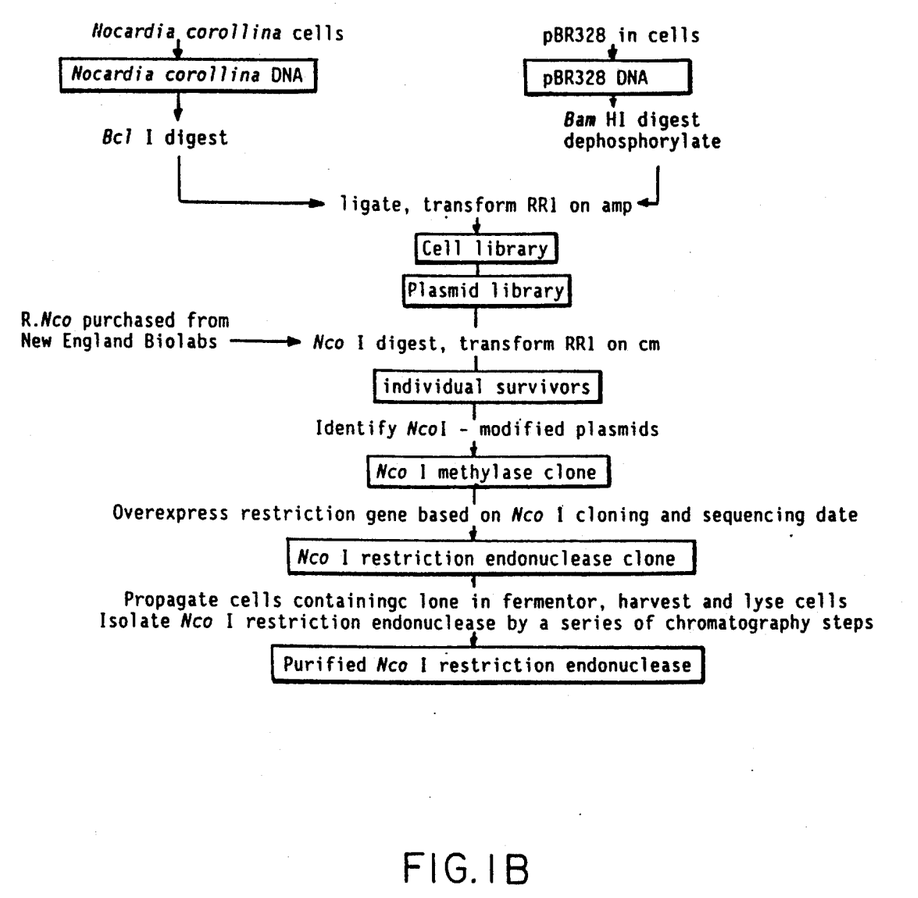
FIG. 1B illustrates the preferred method for cloning and producing the NcoI restriction endonuclease based on actual results presented in FIG. 1A.

The method described herein by which the NcoI restriction gene and methylase gene are preferably cloned and expressed is illustrated in FIGS. 1A and 1B and includes the following steps:

1. The DNA of *N. corallina* is purified.

2 The DNA is digested completely and partially with a restriction endonuclease such as BclI. BamHI, BglII, EcoRI, PstI, Sau3A and XhoII were also used for digestion and for steps 2–7, but since the BclI library was the only library to yield an RM clone, only the details for the BclI work will be described.

3. The digested DNA's are each ligated to a cloning vector, such as pBR328, which contains an NcoI site in its chloramphenicol gene. The resulting mixtures are used to transform an appropriate host such as *E. coli* strain RR1 or K802 cells (ATCC 31343 and ATCC 33526, respectively). RR1 is the preferred host cell.

4. The DNA/cell mixtures are preferably plated on antibiotic media selective for transformed cells, such as ampicillin or chloramphenicol. After incubation, the transformed cell colonies are collected together to form the primary cell libraries.

5. The recombinant plasmids are purified in toto from the primary cell libraries to make primary plasmid libraries.

6. The plasmid libraries are then digested to completion in vitro with the NcoI restriction endonuclease, which is prepared from *N. corallina* cells. NcoI restriction endonuclease digestion causes the selective destruction of unmodified, non-methylase-containing clones, resulting in an increase in the relative frequency of NcoI methylase-carrying clones. Exonuclease and-/or phosphatase may also be added to the digestion to enhance the destruction of non-methylase clones.

7. Identification of NcoI methylase clones: The digested plasmid library DNA's are transformed back into a convenient host such as *E. coli* strain RR1 or K802, and transformed colonies are again obtained by plating on antibiotic plates. DNA from individual colonies is analyzed for the presence of the NcoI modification gene in the following manner: The plasmid DNA that they carry is purified and incubated in vitro with NcoI restriction endonuclease to determine whether it is resistant to digestion by NcoI. The plasmid DNA should be completely or substantially resistant to digestion. The total cellular DNA (chromosomal and plasmid) of the clone is also purified and incubated with NcoI restriction endonuclease. Further proof that the methylase gene has been cloned involves deleting the insert and checking the remaining vector for presence of intact NcoI sites.

8. Once it has been established that the methylase gene has been cloned, the clone is assayed for NcoI restriction endonuclease activity. If activity is detected, then the NcoI restriction gene is linked to the methylase gene and is present in the clone. In such a case one could then skip to step 12 below. However, in accordance with the present invention, it has been found that even if present, the restriction gene is not expressed without further genetic manipulation as discussed below. The lack of restriction activity indicates that either the restriction gene is not linked to the methylase gene, or it is linked but not cloned intact with the methylase gene, or it is cloned intact but not expressed. In order to determine which of the above three possibilities is the true situation, the cloned fragment is restriction-mapped and deletions are made to determine where the methylase gene lies within the cloned fragment. The information is then used to determine if there is enough DNA on either side of the methylase gene to encode a restriction gene, if it were linked. If there is enough room, the restriction gene is assumed to be not linked, or to be present in the clone but not expressed (and one could skip to step 10). If there is not enough room on both sides of the methylase gene in the cloned DNA to encode a linked restriction gene, as was found for the BclI clone of the present invention, a portion of the methylase gene is used to probe digests of the NcoI chromosome to generate a genomic map of the region extending beyond the boundaries of the existing cloned DNA. This data helps identify certain endonucleases that cleave the restriction-modification region into individual fragments that carry the methylase gene as well as larger amounts of adjacent DNA. The exact sizes of the fragments generated by such endonucleases are known from the data as well. Presumably, if the restriction and modification genes are found to be linked, such fragments would also encode the restriction gene.

9. Enriched libraries are constructed by gel-purifying the fragments described in step 8 and ligating them into an appropriate vector such as pBR328. Clones carrying a small amount (2kb or less) of DNA to the left of the methylase gene can be isolated by methylase selection; clones carrying more DNA to the left do not seem to survive methylase selection very well.

10. Identification of restriction gene clones: In accordance with the present invention, it has been found that clones carrying the NcoI restriction endonuclease gene cannot be identified by the usual crude cell extract assay because of the low-level expression of the gene in *E. coli*. Therefore, the NcoI endonuclease is purified as close to homogeneity as possible from *N. corallina*, and the sequence of the first 20-40 amino acids is determined. From the sequence information, a degenerate oligomer DNA probe is designed and radioactively labeled. At the same time the size of the restriction endonuclease protein is determined by protein gels to be about 32 kD, which indicates that the amount of DNA necessary to encode the endonuclease gene is approximately 1 kb for NcoI. Clones carrying the NcoI restriction endonuclease are identified as those that hybridize to the restriction gene DNA probe, and carry at least 1 kb of DNA next to the hybridization location.

11. DNA sequencing of the region confirms the presense of the restriction gene, reveals its orientation, and provides data to use as a basis for subsequent manipulations of the recombinant plasmid to induce expression of the cloned restriction gene in *E. coli*.

12. Production: In one preferred embodiment the NcoI methylase or endonuclease may be produced from transformed host cells transformed with one or more plasmids clones carrying the NcoI modification gene and the overexpressed restriction gene by propagation in a fermenter in a rich medium containing ampicillin and chloramphenicol. The cells are thereafter harvested by centrifugation and disrupted by sonication to produce a crude cell extract containing NcoI methylase and restriction endonuclease activity. In another preferred embodiment, the host cell can be pre-protected by transformation with plasmids carrying the methylase gene followed by introduction of one or more plasmids carrying the endoculease gene.

13. Purification: The crude cell extract containing the NcoI methylase and endonuclease is purified by standard product purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE I

Cloning of Nco I Modification Methylase and Restriction Endonuclease Genes

1. DNA purification: To prepare the DNA of *N. corallina*, 2 gm of cell paste was resuspended in 5 ml of 0.1M Tris-HCl, 0.1M EDTA pH 8. The suspension was divided into two 2.5 ml portions. 3.5 ml of 1.7 mg/ml lysozyme in 0.1M Tris-HCl, 0.1M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. 6 ml of lytic mix was added (50 mM Tris, 62.5 mM EDTA, 1% Triton-X-100, pH 8) and the mixture was incubated at 37° C. for 1 hour. The mixture was then phenol extracted then phenol-chloroform extracted, followed by dialysis against four changes of DNA buffer (10 mM Tris-HCl, 1 mM EDTA pH 8.0) for 24 hours. RNAse was added to 200 μg/ml and incubated at 37° C. for 1 hour. The DNA was then precipitated by adding NaCl to 0.5M and layering 0.55 volume isopropyl alcohol on top. The precipitated DNA was spooled onto a glass rod. The DNA was dissolved in 1 ml 10mM Tris, 1 mMEDTA (pH 8) to a final concentration of approximately 400 μg/ml.

NOTE FOR STEPS 2-10: As noted above, 7 different endonucleases were each used to digest the Nco chromosome to construct and screen libraries. Since the methylase gene did not express well enough to survive selection in all cases except BclI (and Sau3A, which clone was a subset of the BclI clone) only the details for the BclI library will be provided. The other libraries were prepared by methods similar to those outlined below.

2. Complete and partial digestion: The purified DNA was cleaved with BclI to achieve partial digestion as follows: 375 μl containing 46.5 μl of DNA at 400 μg/ml in 10 mM Tris pH 7.5, 10 mM MgCl$_2$, 50 mM NaCl, 10 mM mercaptoethanol buffer was divided into one 150 μl aliquot and three, 75 μl aliquots. To the 150 μl tube was added 10 units of BclI to achieve 1.3 units of enzyme per μg of DNA. 75 μl was withdrawn from the first tube and transferred to the second tube to achieve 0.65 units BclI/μg, and so on, each succeeding tube receiving half of the previous amount of BclI. The tubes were incubated at 37° C. for one hour, then heat-treated at 72° C. for 15 minutes and 10 μl from each was analyzed by agarose gel electrophoresis. Tubes 3 and 4 exhibited moderately incomplete as well as completely digested DNA; these two tubes were combined and used as described in step 3 below.

3. Ligation: The fragmented DNA was ligated to pBR328 as follows: 2 μg of BclI-completely-and-partially digested N. corallina DNA (40 μl) were mixed with 1 μg of BamHI-cleaved and dephosphorylated pBR328 (2.5 μl). 20 μl of 10X ligation mix (500 mM Tris, pH 7.5, 100 mM MgCl$_2$, 100 mM DTT, 5 mM ATP) was added, plus 137.5 μl of sterile distilled water to bring the final volume to 200 μl. 7.5 μl of T4 DNA ligase (400u/μl) was added and the mixture was incubated at 16° C. for 4 hours. Approximately 125 μl of the ligated DNA was used to transform E. coli strain RR1 as follows: The DNA was mixed with 1.0 ml of SSC/CaCl$_2$ (50 mM NaCl, 5 mM Na$_3$ Citrate, 67 mM CaCl2) on ice and 2.0 ml of ice-cold competent E. coli RR1 (hsd R-M-, ATCC No. 31343) cells were added. After a 5-minute incubation at 42° C., the cells were diluted by the addition of 8 ml of Luria-broth (L-broth) then incubated at 37° C. for 1 hour. 4. Primary Cell Library: The transformed cell culture was briefly centrifuged, the supernatant was discarded and the cells were resuspended in 0.6 ml of L-broth. 200 μl portions were plated onto Luria-agar (L-agar) plates containing 100 μg/ml ampicillin. After overnight incubation at 37° C., the plates were each flooded with 2.5 ml of 10 mM Tris, pH 7.5, 10 mM MgCl$_2$ and the transformed colonies were scraped together and pooled to form the primary cell library.

5. Primary Plasmid Library: The primary plasmid library was prepared as follows: 2.5 ml of the primary cell library was inoculated into 500 ml of L-broth containing 100 μg/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5 ml of 0.25 M EDTA, pH 8.0, was added, followed by 3 ml of 10 mg/ml lysozyme in 0.25 M Tris, pH 8.0. The solution was left on ice for 3 hours, then 12 ml of lytic mix (1% Triton X-100, 50 mM Tris, pH 8.0, 67 mM EDTA) was forcefully pipetted in, and the cell suspension gently swirled to achieve lysis. After lysis, the mixture was transferred to a 50 ml plastic centrifuge tube and spun at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two 5/8 in. ×3 in. polyallomer centrifuge tubes and sealed. These tubes were then spun in a Beckman Ti70 rotor for 42 hours at 44000 rpm, 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15000 rpm, 0° C. for 15 minutes and the supernatant discarded. The tube was left on the bench to air-dry for 15 minutes, then the DNA pellet was dissolved in 500 μl of DNA buffer and stored at −20° C. The DNA concentration of plasmids prepared in this way were found to be 200 to 300 μg/ml.

6 Digestion of Plasmid Pool: The primary plasmid pool was digested to destroy non-NcoI methylase clones as follows: The plasmid DNA was diluted to 33 μg/ml in 10 mM Tris pH 8.0, 10 mM MgCl$_2$, 150 mM NaCl. A total of 900 μl was prepared. 450 μl was placed in tube 1, 225 μl in each of tubes 2 and 3. 8 u/μg NcoI (120 units) was added to tube 1 and mixed; 225 μl was transferred to tube 2 to achieve 4 u/μg. Tube 3 received no NcoI. Tube 1 was incubated at 37° C. for 3.5 hours then treated with lambda exonuclease, tubes 2 and 3 were incubated for 1 hour.

7 Transformation: A 12.5 μl sample from each tube was used to transform E. coli RR1. After the 3-minute heat step and 1 hour of growth in luria broth at 37° C., the cell/DNA mixtures were plated onto L-agar plates containing 200 μg/ml chloramphenicol. After overnight incubation at 37° C., the plates were examined. Ten individual colonies were picked from each of the 8 and 4 u/μg plates. Each colony was inoculated into 10 ml of L-broth containing chloramphenicol, to prepare a miniculture, and was also streaked onto L-agar plates containing chloramphenicol to prepare a master stock.

8. Analysis of surviving individuals: 20 of the surviving colonies obtained from step 7 were grown up into 10 ml cultures (step 7) and the plasmids that they carried were prepared by the following miniprep purification procedure, adapted from the method of Birnboim and Doly (Nucleic Acids Res. 7: 1513 (1979)).

Miniprep Procedure: Each culture was centrifuged at 8000 rpm for 5 minutes; the supernatant was discarded and the cell pellet was resuspended in 1.0 ml of 25mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 µl of 10 mM Tris, 1 mM EDTA, pH 8.0. 75 µl of 5M NaCl was added to each and the solutions were transferred to Eppendorf tubes containing 575 µl of isopropanol, and again precipitated for 10 minutes at room temperature. The tubes were then spun for 45 seconds in a microfuge, the supernatants were discarded and the pellets were air-dried. The pellets were then dissolved in 500 µl of 10 mM Tris, 1 mM EDTA, pH 8.0, containing 100 µg/ml RNAse and incubated for 1 hour at 37° C. to digest the RNA. The DNA was precipitated once more by the addition of 50 µl of 5M NaCl followed by 350 µl of isopropanol. After 10 minutes at room temperature, the DNA was spun down by centrifugation for 45 seconds, the supernatants were discarded and the pellets were redissolved in a final solution of 150 µl of 10mM Tris 1 mM EDTA, pH 8.0. The plasmid minipreps were subsequently analyzed by digestion with NcoI.

9. Methylase Gene Clones (pEV190RM612-22C): 4 plasmids (from the 4 u/µg plate) were found to be resistant to NcoI and to carry a 6.6 kb fragment comprised of two BclI fragments, 1.5 and 5.1 kb in size (see FIG. 2). In each case the 6.6 kb fragment was in the same orientation with respect to the plasmid's tetracycline-resistance-gene promoter. These 4 plasmids were subsequently shown to carry the NcoI modification methylase gene. This was established by deleting the BclI inserts and checking the remaining vector for intact, cleavable NcoI site, and by purifying the chromosomal DNA from the clone and proving that it is modified by NcoI, that is, resistant to NcoI digestion. Both BclI fragments (1.5 and 5.1 kb) were found to be required for methylation.

10. The extract was assayed for restriction endonuclease activity; none was detected. The crude cell extract was concentrated over a phosphocellulose column, but still no activity was detected.

11. Location of the methylase gene within the 6.6 kb BclI insert: The NcoI methylase clone was digested with numerous restriction endonucleases to provide a restriction map of the cloned DNA. Using the map, various regions within the insert were deleted to determine the resulting affect on methylation. The location of the 1 kb methylase gene within the 6.6 kb insert was then pinpointed, and the length of cloned DNA on either side of the gene was found to be between about 1 and 4 kb. The 4 kb on the right of the M gene was considered to be enough room to encode a linked R gene, but the 1 kb on the left side was not considered sufficient room to encode a linked restriction endonuclease gene. At this point, the distance between the two genes, the exact size of the genes, and whether or not they were linked was not known. The lack of NcoI endonuclease activity in the clone indicated that the restriction gene was either not present in the clones, or was present but not expressed. In the event that the restriction gene was present and not expressing, DNA sequencing and protein sequencing of the methylase clones were undertaken to determine whether part, all or none of the restriction gene was present in the clones (steps 15-16). In the event that the entire restriction gene was not present, the cloning of larger regions of DNA adjacent to the methylase gene Was achieved as follows (steps 12-14).

12. A genomic map of the adjacent regions was determined using the southern blot technique (Southern, E. 1975, J.Mol.Bio., 98:503) and a portion of the methylase clone as a probe, specifically, approximately 1 kb BamHI-ScaI fragment gel-purified and labeled with alpha $^{35}$S-ATP. Gel-purification is described below in step 13 (with two modifications: the final volume was 20 µl; and drop-dialysis was not done). The gel-purified probe was labeled using Pharmacia's oligolabeling kit (lot QE106638): 2 µl fragment (0.1 µg) in 30 µl dH20 was heated to 90° C. for 15 minutes, then 5 minutes at 37° C. 10 µl reagent mix, 2 µl BSA, 4 µl $^{35}$S (50 µCi), and 2 µl klenow were added and the mixture was incubated overnight at room temperature. 20 µl stop buffer and 180 µl dH20 was added. The mixture was then boiled for 10 minutes and placed immediately on ice.

The southern blot was prepared as follows: N. corallina DNA was digested separately with the restriction endonucleases AccI, BamHI, BglII, ClaI, EcoRI, EcoRV, FspI, HindIII, NruI, PstI, PvuII, SalI, and SspI. The digests were electrophoresed on a 1.0% agarose gel. The gel was soaked in 0.25M HCl for 10 min; 0.4M NaOH, 0.8M NaCl for 30 min; and then in 0.5M Tris.HCl pH 7.5, 1.5M NaCl for 30 min. A nitrocellulose sheet was soaked briefly in water, then in 5×SSC (0.75M NaCl, 75 mM Na3Citrate). The gel was placed on top of a ¼ inch stack of chromatography paper (Whatman) in 300 ml 3M NaCl, 0.3M Na3Citrate buffer, with the level of buffer just below the height of the stacked paper. The nitrocellulose sheet was placed on top of the gel and backed with chromatography paper (Whatman) to act as a wick. The sandwich was weighted down and transfer of the gel contents to the nitrocellulose sheet was allowed to proceed at room temperature overnight. The sheet was then rinsed in 0.15M NaCl, 15mM Na3Citrate for ten minutes and baked in a vacuum oven at 80° C. for 2.5 hours to fix the transferred DNA fragments to the nitrocellulose. The sheet was transferred to a tray containing 100 ml of a solution composed of 5 ml 0.03M Tris, 0.001M EDTA, pH 7.5, sterile; 25 ml 20×SSC (3M NaCl, 0.3M Na3Citrate), 50 ml formamide, 10 ml 10% SDS, 10 ml 100×Denhardt's (20 gm/L Ficoll, 20 gm/L polyvinylpyrrolidone, 20 gm/L bovine serum albumin). Calf-thymus DNA was boiled for 10 minutes then cooled on ice, then added to the mixture to 0.05 mg/ml. The blot was prehybridized by incubating at 37° C. shaking for 5 hr. 240 µl radioactive probe was added to the tray, and incubation was continued at 37° C. shaking overnight. The nitrocellulose sheet was then washed four times for 5 minutes each at room temperature with 0.015M NaCl, 1.5mM Na3Citrate, 0.1% SDS; once for twenty minutes at 55° C. in the same buffer, and once in 0.15M NaCl, 15 mM Na₃Citrate for twenty minutes at room temperature. The sheet was then air-dried, dried for 1 hour in vacuum oven at 80° C., and autoradiographed five days.

From the southern blot data, the sizes of eight methylase-encoding fragments were known. Attempts to clone the 5.5 kb ClaI, the 3.8 kb FspI, the 6 kb PvuII, the 8 kb PstI and the 3 kb SalI fragments were undertaken. The other three known fragments (BamHI, NruI, AccI) were not pursued, and the remaining bands were judged to be too large to clone.

13. Initially, three libraries (ClaI, FspI, and PvuII) were constructed and selected by the same procedures as steps 1–8 with the following modifications at steps 2 & 3: 60 μl (30μg) NcoI chromosomal DNA was digested completely in 300 μl 10 mM Tris pH7.5, 10 mM MgCl₂, 50 mM NaCl, 10 mM mercaptoethanol containing 75 units of ClaI, 38 units of FspI, or 150 units of PvuII at 37° C. for 2 hours. The entire volume was electrophoresed in a 1% agarose gel containing 0.01% SDS for 5 hours. Using long wave UV to view the gel, the fragments within the size range of the known size of the methylase-gene-carrying fragment were cut out of the gel and minced with a clean razor blade. The mixture was forced through a 22-gage syringe into 5 ml 1×agarose gel buffer containing 0.01% SDS, and centrifuged 17 krpm 45 minutes. The supernatant was precipitated with 0.5ml 5M NaCl and 1.1 ml isopropanol at −20° C. overnight. The DNA was pelleted 15 krpm, 15 minutes. The pellet was resuspended in 500 μl 10 mM Tris pH8, 1 mM EDTA, phenol/chloroform extracted, chloroform extracted three times and precipitated again with 48 μl 5M NaCl and 1100 μl isopropanol at −20° C. three hours. The pellet was rinsed with 70% isopropanol and air dried, and resuspended in a final volume of 100 μl 10 mM Tris pH8, 1 mM EDTA. To further purify the fragments, the 100 μl was drop-dialysed for 30 minutes on a millipore VS 0.025 μM filter floating on top of 10 mM Tris, 1 mM EDTA, pH8.

15 μl (0.5 μg) of FspI or PvuII DNA fragments were ligated to 1.2 μl (0.25 μg) of EcoRV-cleaved and dephosphorylated pBR328 in 70 μl 1×ligation buffer containing 3 μl concentrated T4 DNA ligase (6000 units) at 16° C. 4 hours. 40 μl (1 μg) ClaI DNA was ligated to 1.8 μl (0.5 μg) ClaI-cleaved pBR328 in 70 μl 1×ligation buffer containing 1.2 μl (2400 units) concentrated ligase at 16° C. for 4 hours then room temperature overnight. All 70 μl was transformed into RR1.

Figure 3:
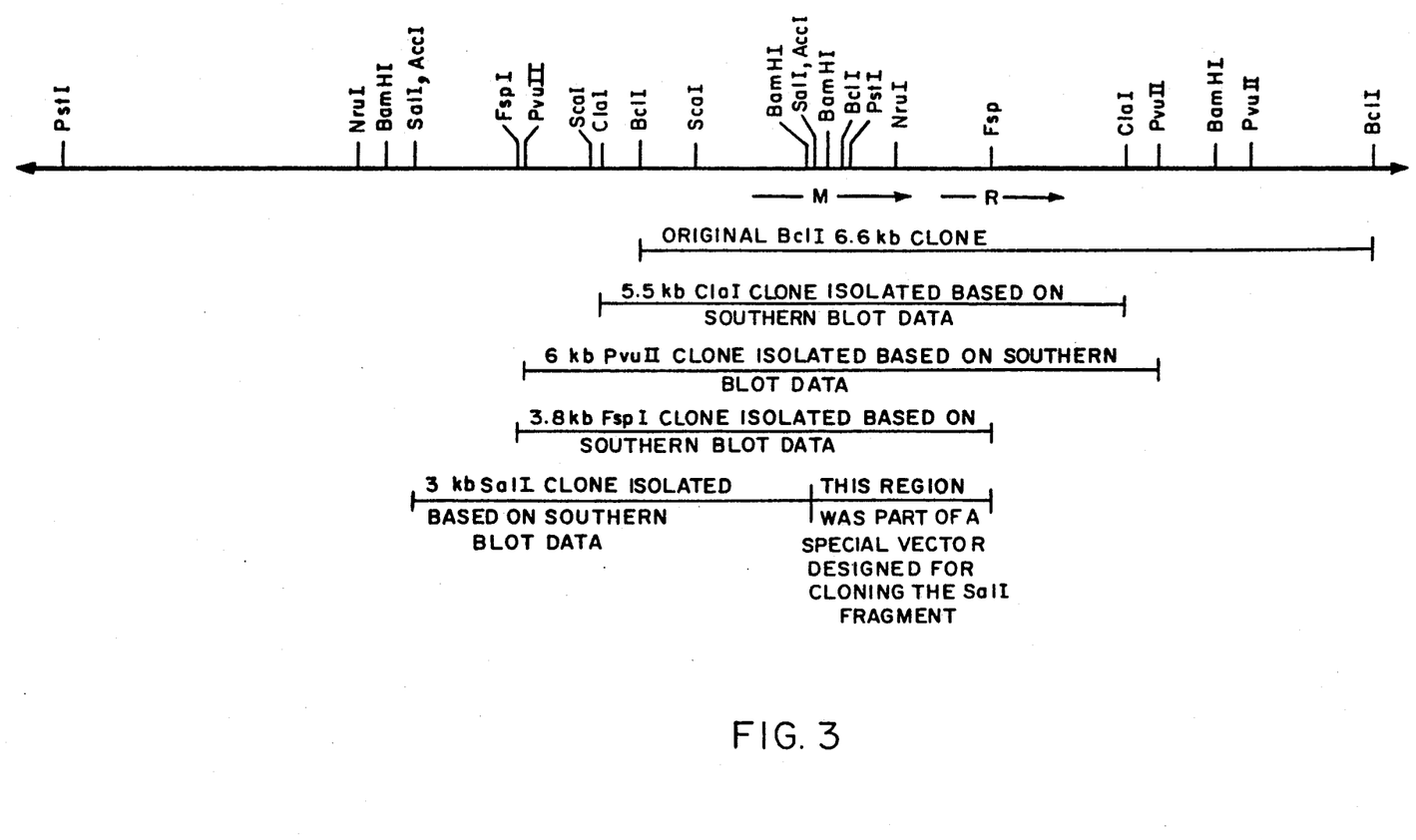
FIG. 3 is a restriction map of the entire 8 kb of *N. corallina* DNA that has been cloned.
Figure 4:
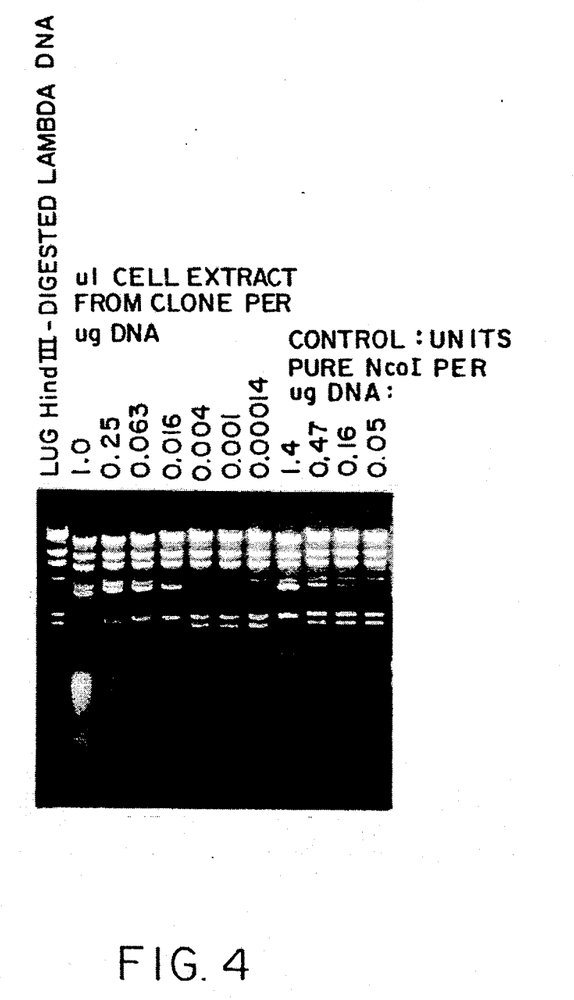
FIG. 4 is a photograph of an agarose gel illustrating NcoI restriction endonuclease activity obtained from the cell extract of *E. coli* ER1451 containing pEV190R612-22C-29, which is a plasmid carrying the cloned and reconstructed endonuclease gene, and pEV190M302,325-1, which is a plasmid carrying the cloned methylase gene.

14. Identification of new ClaI, FspI, PvuII methylase clones carrying a larger region of DNA upstream from the methylase gene: The only ClaI survivor from step 13 was found to carry the 5.5 kb ClaI methylase-encoding (M+) fragment; 7 of 8 FspI survivors were found to carry the 3.8 kb FspI M+ fragment, and 9 of 12 PvuII survivors were found to carry the 6 kb PvuII M+fragment. These clones overlapped the original BclI clone as indicated in FIG. 3 and, when in line with the plasmid's promoter, were found to be fully modified. No restriction endonuclease activity was detected.

The new clones, which carried >1.3 kb DNA upstream of the M gene, were believed to possibly, but not certainly, be enough DNA to encode a 1 kb restriction endonuclease gene if it were linked upstream of the methylase gene. Therefore, attempts to clone the 3 kb SalI and the 8 kb PstI fragments were pursued, as the SalI and PstI clones would carry larger amounts of upstream DNA. Special vectors had to be constructed to clone these fragments, as they carry only half of the M gene. The vectors were designed to carry the other half, such that when the desired fragment was ligated into the cloning vector, the M gene was reformed and the plasmid was able to modify itself and survive methylase selection.

The SalI clone, which carries ≧2 kb DNA upstream of the M gene, was found to be only partially modified. This is believed to be due to an increased distance of the M gene from the plasmid's promoter. Consistant with this belief is the observation that the PstI fragment was not cloned, probably because the PstI fragment carries about 7 kb upstream DNA, placing the M gene even further from the plasmid promoter. Such a plasmid would probably not express the M gene well enough to modify itself, and would not survive methylase selection easily. Nevertheless, attempts to clone the PstI fragment were not pursued because the SalI clone was believed to carry enough room (>2 kb) to encode the R gene, if it were linked upstream of the M gene.

15. With the recovery of the new clones, there was now enough DNA cloned on both sides of the methylase gene to encode a restriction endonuclease gene, if it were linked, regardless of which side encoded the linked gene. However, none of the clones expressed any restriction endonuclease activity. With still no proof that the two NcoI restriction-modification genes were linked, the NcoI restriction endonuclease was purified as close to homogeneity as possible as follows:

After breakage of 566 grams *N. corallina* by French press, the 2.2 liter supernatant was placed over chromatography columns in the following order: DEAE-cellulose, heparin-sepharose, phosphocellulose, DEAE-cellulose, phosphocellulose, polyCAT A FPLC, mono Q FPLC and mono S FPLC. The resulting preparation was greater than 95% pure NcoI restriction endonuclease, with a size of about 32,000 daltons as determined by SDS-PAGE electrophoresis.

Approximately 33 μl (1.5 μg, 50 pmol) of the purified NcoI restriction endonuclease was applied to three lanes of a SDS-polyacylamide 10–20% gradient gel and subjected to electrophoresis at 100 volts for 3 hours. The gel was then electroblotted to a PVDF (Immobilon, Millipore) membrane at 200 mA for 12 hours (Matsudaira, 1987). The membrane was stained with Coomassie Blue R-250 and the middle band corresponding to the NcoI restriction endonuclease was excised with a razor blade. The bands were multiply-sliced at 0.5 mm intervals to a comb-like appearance, to maximize the efficiency of wetting by the sequenator reagents. The bands were used for sequencing on an Applied Biosystems Model 470A gas phase protein sequencer using a 120A online HPLC for PTH detection. Thirty amino acid residues were sequenced as follows: alanine—threonine—alanine—proline—glycine—histidine—leucine—leucine—glycine—glutamine—isoleucine —isoleucine—glycine—asparagine—valine—methionine—glutamic acid—glutamic acid—alanine —leucine—lysine—proline—valine—leucine—glutamine—glutamic acid—methionine—alanine—aspartic acid—arginine.

16. Identification of restriction gene clones: Based on the above sequence, a 17-mer DNA oligo probe with 32-fold degeneracy was constructed by the Organic Synthesis Division of New England Biolabs:

AA(C,T)GTNATGGA(G,A)GA(G,A)GC where N=G,A,T or C.

Only several amino acid residues were chosen for translation into DNA sequence because their DNA sequence had the least degeneracy.

The original BclI clone carrying about 4 kb DNA downstream of the M gene, and the subsequent SalI clone carrying about 2 kb DNA upstream of the M gene, were digested with various restriction endonucleases and blotted onto nitrocellulose like the procedure described above (step 12). The DNA 17-mer was kinased in 26 μl as follows: 2.5 μl 10 X kinase buffer (700 mM Tris-Hcl pH7.6, 100 mM $MgCl_2$, 50 mM DTT, 2.6 mM 5'-hydroxyl-terminated salmon sperm DNA), 5 μl 14-mer (1 O.D./ml), 12.5 μl dH20, 5 μl gamma P32ATP (50 uCi), and 1 μl kinase (10 units), at room temperature for 1.3 hours. The entire volume was added to the pre-hybridized blot and shaken overnight at room temperature. The blot was washed and exposed as described in step 12. The results showed that the oligomer hybridized to a specific location on the BclI and SalI clones, allowing the location of the beginning of the NcoI restriction endonuclease gene to be pinpointed to within a particular 300 base pair region in the cloned DNA (see FIG. 2: the oligomer hybridized in between the NruI and MscI sites). This was indirect but substantial proof that the NcoI restriction-modification genes are linked and completely cloned together on the BclI clone and partly on the SalI clone.

Figure 2:
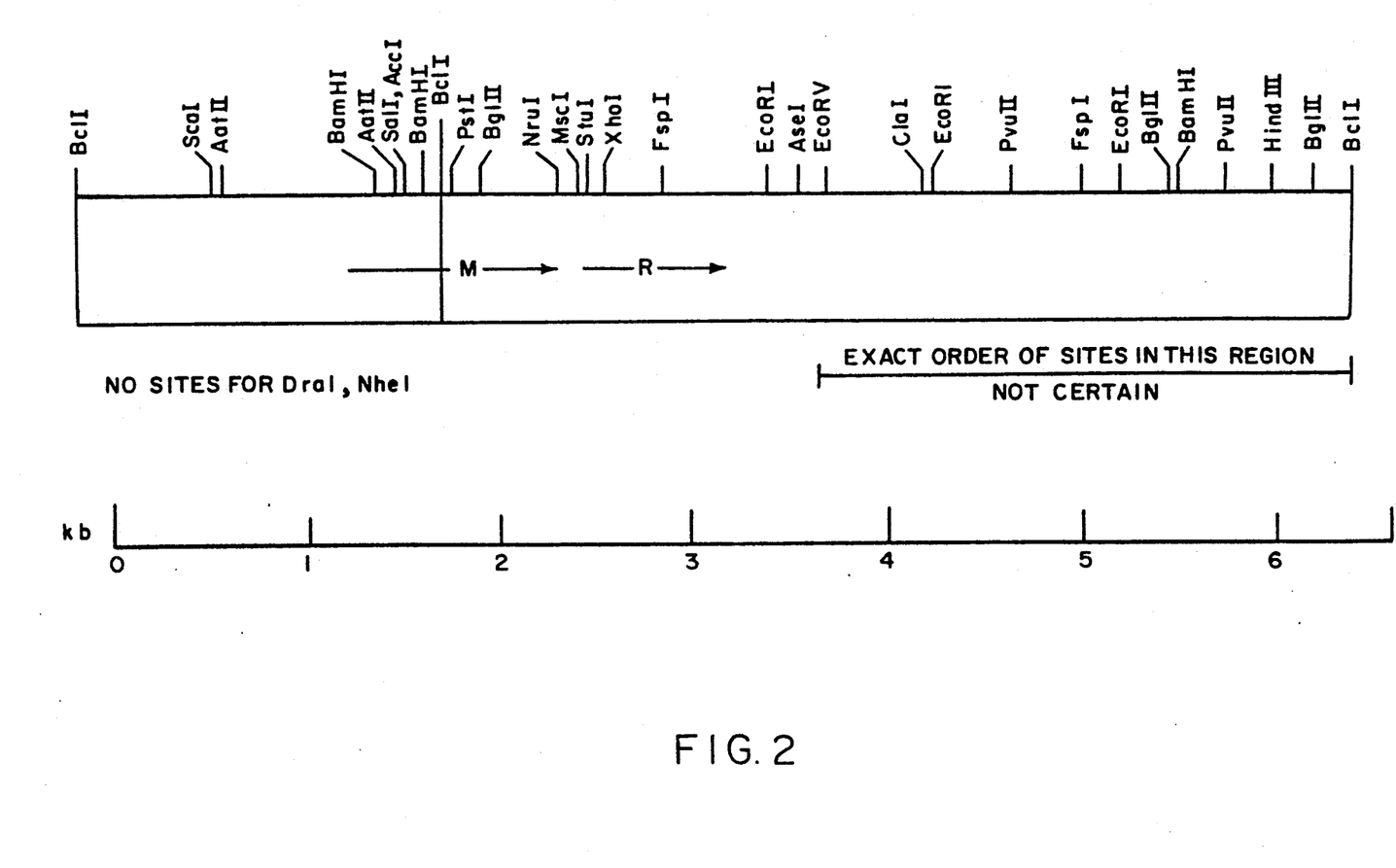
FIG. 2 is a restriction map of the original 1.5 and 5.1 kb BclI inserts that encode the NcoI methylase and endonuclease.

17. DNA sequencing confirmed the presence of the R gene and revealed that it is oriented as indicated in FIGS. 2 and 3.

18. Overexpression: Placing the strong promoter pL 500 bp in front of the restriction gene did not lead to expression. Therefore, the DNA at the start of the restriction endonuclease was sequenced, and the information was used to reconstruct the beginning of the R gene to change its naturally occurring GTG start to an ATG start, as ATG is more easily utilized by E. coli. The RBS (ribosomal binding site) and promoter were also replaced with ones that are recognized by E. coli. The reconstructed R gene pEV190R 612-22C-29 was identified by transformation into AP1 200 cells (these cells were found to turn blue in the presence of X-gal if the R gene expresses). The plasmid was then transformed into strain ER1451 containing pEV190M302,325-1. pEV190M302,325-1 plasmid contains the cloned NcoI methylase gene and pre-modifies ER1451. A sample of ER1451 containing both plasmids has been deposited at the American Type Culture Collection on Nov. 1, 1990 under ATCC Accession No. 68457. In ER1451, maximum activity (500,000 units per gram) is obtained when IPTG is added. The overexpressed R gene, it was discovered, cannot be transformed into strain RR1, even if pre-modified by the NcoI methylase, as RR1 is not regulated by IPTG and the levels of activity are toxic.

19. The NcoI modification methylase or endonuclease may be produced from clones carrying the NcoI modification gene and the overexpressed restriction gene by propagation in a fermenter in a rich medium containing ampicillin and chloramphenicol. The cells are thereafter harvested by centrifugation and disrupted by sonication to produce a crude cell extract containing NcoI methylase and restriction endonuclease activity.

20. The crude cell extract containing the NcoI methylase and endonuclease is purified by standard product purification techniques such as affinity-chromatography, or ion-exchange chromatography.

What is claimed is:

1. Isolated DNA coding for the NcoI restriction endonuclease, wherein the isolated DNA is obtainable from the vector pEV19OR612-22C-29.

2. A recombinant DNA vector comprising a vector into which a DNA segment coding for the NcoI restriction endonuclease produced by Nocardia corallina ATCC 19070 has been inserted.

3. Isolated DNA coding for the NcoI restriction endonuclease and methylase, wherein the isolated DNA is obtainable from ATCC Accession No. 68457.

4. A cloning vector comprising the isolated DNA of claim 1 or 3.

5. A host cell transformed by the cloning vector of claim 4.

6. A method of producing NcoI restriction endonuclease comprising culturing a host cell transformed with the vector of claim 2 or 4 under conditions suitable for expression of NcoI restriction endonuclease.

* * * * *